United States Patent
Ruhe, Jr.

(10) Patent No.: US 6,958,409 B1
(45) Date of Patent: Oct. 25, 2005

(54) PROCESS FOR REDUCED CRUDE SEDIMENT IN METAL SALTS OF HYDROCARBYL DITHIOPHOSPHORIC ACID

(75) Inventor: William R. Ruhe, Jr., Benicia, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 10/869,257

(22) Filed: Jun. 15, 2004

(51) Int. Cl.[7] .................. C07F 9/16; C10M 137/06
(52) U.S. Cl. .................. 556/25; 508/371; 508/379
(58) Field of Search .................. 556/25; 508/371, 508/379

(56) References Cited

U.S. PATENT DOCUMENTS

| | | | |
|---|---|---|---|
| 3,290,347 A | 12/1966 | Miller | |
| 3,347,790 A | 10/1967 | Mainhardt | |
| 3,562,306 A | 2/1971 | Blaha et al. | |
| 3,573,293 A | 3/1971 | Wiese | |
| 3,836,745 A | 9/1974 | Costello | |
| 3,854,530 A | 12/1974 | Jouet et al. | |
| 4,085,053 A | 4/1978 | Caspari | |
| 4,092,341 A | 5/1978 | Lowe et al. | |
| 4,308,154 A | 12/1981 | Clason et al. | |
| 4,377,527 A | 3/1983 | Sabol et al. | |
| 4,456,538 A * | 6/1984 | Ripple | 508/379 |
| 4,507,215 A | 3/1985 | Schroeck | |
| 4,577,037 A * | 3/1986 | Buckley | 556/25 |
| 4,778,906 A * | 10/1988 | Love et al. | 556/25 |
| 4,882,446 A * | 11/1989 | Born et al. | 556/25 |
| 5,380,448 A | 1/1995 | Kadkhodayan et al. | |
| 5,384,054 A | 1/1995 | Kadkhodayan | |
| 5,627,294 A | 5/1997 | Adams et al. | |
| 5,728,656 A | 3/1998 | Yamaguchi et al. | |

\* cited by examiner

*Primary Examiner*—Porfirio Nazario-Gonzalez
(74) *Attorney, Agent, or Firm*—Joseph P. Foley; Claude J. Caroli

(57) ABSTRACT

A process for the manufacture of a low sediment overbased metal dithiophosphate composition is disclosed. The process uses delayed addition of a $C_1$ to $C_5$ mono-carboxylic acid promoter during the neutralization of a primary dialkyl dithiophosphoric acid. The process results in reducing crude sediment whereby the resulting overbased metal dithiophosphate may need not undergo additional filtration steps prior to its intended use.

26 Claims, No Drawings

PROCESS FOR REDUCED CRUDE SEDIMENT IN METAL SALTS OF HYDROCARBYL DITHIOPHOSPHORIC ACID

FIELD OF THE INVENTON

The present invention relates to a process for the manufacture of a low crude sediment overbased metal dithiophosphate composition prepared by delaying the addition of an acidic promoter. The process results in reducing crude sediment and haze of the product; whereby the resulting overbased metal dithiophosphate may need not undergo filtration prior to its intended use.

BACKGROUND OF THE INVENTION

Metal diaryl and dialkyl dithiophosphates, especially zinc dithiophosphate, have long been used as antiwear additives and antioxidants in hydraulic oils, motor oils, automatic transmission fluids and the like. Processes for the production of these compounds are also well-known. In the manufacture of such metal dithiophosphates, dithiophosphoric acid is commonly neutralized with a metal base, such as zinc oxide. This neutralization step does not take place readily and commonly a large excess of the base is used; and sometimes in conjunction with a promoter. Promoters used for this purpose have varied widely. U.S. Pat. No. 3,562,306 discloses an inorganic zinc salt may act as a promoter. Ammonia and other amines have also been disclosed to act as promoters see for example U.S. Pat. Nos. 3,573,293; 3,836,745; 4,377,527 and 4,377,527. Acid promoters have also been disclosed, such as strong acid (hydrochloric, perchloric or nitric), sulfonic acids and carboxylic acids, see for example U.S. Pat. Nos. 3,347,790; 3,290,347 and 4,085,053. Where the latter employs an acidic promoter followed by a weak base. Nitrogen dioxide has been suggested as a promoter in U.S. Pat. No. 4,092,341.

As known in the art, promoter use can have undesirable side effects. Use of some promoters can lead to a product which may have stability issues, have relatively high sediments, have difficultly filtering, have a dark color and/or have an unacceptable haze. While certain promoters can improve crude sediment levels, the crude sediment levels remain sufficiently high so that filtration is required. Typically, in conjunction with filtration additional components are used to reduce the sediment and haze to more acceptable levels. However, the use of these additional components has drawbacks. Preferably, process conditions could avoid the need for additional components. Surprisingly, it has been discovered that a process employing a controlled delayed addition of a particular class of promoters during neutralization of a dialkyl dithiophosphoric acid derived from primary alcohol and subsequent overbasing yields a low sediment, low haze, overbased metal dithiophosphate composition.

SUMMARY OF INVENTION

Disclosed is a process for the manufacture of a low sediment overbased metal dithiophosphate composition prepared by employing a delayed addition of a mono-carboxylic acidic promoter. The delayed addition of the promoter in the particular process results in reducing crude sediment and producing a low haze product, whereby the resulting overbased metal dithiophosphate may need not undergo filtration prior to its intended use. Therefore, one embodiment of the present invention is directed to a process for the manufacture of a low sediment overbased metal dialkyl dithiophosphate composition comprising:

a) reacting a phosphorous sulfide reactant with at least one $C_3$ to $C_{12}$ primary alcohol to form a dialkyl dithiophosphoric acid;

b) neutralizing the dialkyl dithiophosphoric acid with a full charge of metal oxide for a sufficient amount of time, to form an intermediate product comprising basic and neutral dialkyl dithiophosphate salts, said intermediate product characterized as having a ratio of basic salt to neutral salt of about 0.075 to about 0.75, wherein said ratio is determined by $^{31}$P-NMR analysis;

c) adding to the intermediate product from 1.5 to 5 weight percent based upon the metal oxide charge, of at least one aliphatic mono-carboxylic acid promoter having 1 to 5 carbon atoms to form a reaction mass; and d) reacting the reaction mass under suitable temperature and time to form an overbased metal dialkyl dithiophosphate product characterized as having a crude sediment before filtration of 0.01 weight percent or less.

Quite unexpectedly, delaying the addition of the promoter until a particular point in the neutralization step leads to an overbased metal dialkyl dithiophosphate product having low crude sediment and low haze. The promoter is delayed until such a point, so that an intermediate product is characterized as having a ratio of basic salt to neutral salt of greater than about 0.075, typically from 0.075 to about 0.75, and preferably the ratio of basic to neutral salts of intermediate dialkyl dithiophosphate is from 0.1 to 0.5 and even more preferably from 0.1 to 0.3 as determined from $^{31}$P-NMR. Particularly preferred salts above are zinc salts prepared from a zinc oxide. Particularly, the dialkyl dithiophosphate is derived from the reaction of a phosphorous sulfide reactant with at least one $C_3$ to $C_{12}$ primary alcohol. Preferably the phosphorus sulfide is a phosphorous pentasulfide selected to have a phosphorus weight percent from 27.9 to 28.3.

Not all metals oxides are suitable for neutralization or lead to forming overbased metal dialkyl dithiophosphate compositions. Accordingly, in one embodiment the metal of the metal oxide is selected from the group consisting of bismuth, cobalt, chromium, copper, nickel, vanadium, tungsten and zinc; with zinc oxide being particularly preferred. The metal oxide is preferably a dry powder having a "high surface area" meaning for example, that if zinc oxide is employed, it has a surface area of greater than about 3 $m^2$ per gram, preferably from about 4 to about 10 $m^2$ per gram or alternatively a superfine or nanoparticle zinc oxide having 11 to 40$m^2$ per gram.

The process of the present invention need not employ diluent oil or process water as a slurry medium for the suspension the metal oxide used in the neutralization step, and preferably neither is employed. The metal oxide is typically fed directly to the neutralization reactor. If the metal oxide is to be slurried, preferably it is slurried in a portion of the total amount of dialkyl dithiophosphoric acid used in the process. Therefore, the dialkyl dithiophosphoric acid not only serves as a slurry medium; thus, not requiring the use of excess diluent oil or process water to administer the metal oxide to the reaction mass, but subsequent to reaction it can serve as a process heat sink, while not reducing reactor capacity with the addition of unnecessary inert materials. The amount of dialkyl dithiophosphoric acid used to slurry the metal oxide is not critical to the invention, but will normally be in the range of 20 to about 40 weight percent of the total dialkyl dithiophosphoric acid charge and more preferably, from about 30 to 35 weight percent of the total dialkyl dithiophosphoric acid charge. The remaining portion of the dithiophosphoric acid used in the neutralization step is then added to the resulting slurry over a period of time typically ranging from about one hour to three hours. Most preferably, the full charge of dialkyl dithiophosphoric acid can be added to the reactor prior to the addition of the metal oxide, with a particularly preferred metal oxide as stated above being zinc oxide. The rate of metal oxide addition is such that the charge time to the reaction mass is less than about 60 minutes and preferably less than 30 minutes.

Thus, another embodiment of the invention is directed to a process for the manufacture of a low sediment overbased zinc dialkyl dithiophosphate composition having a zinc to phosphorous weight ratio of from 1.08 to 1.30 comprising:

a) forming a slurry of a full charge of zinc oxide in a full charge of a dialkyl dithiophosphoric acid derived from the reaction of phosphorous pentasulfide and at least one $C_3$–$C_{12}$ primary alcohol;

b) reacting the slurry in a) under suitable conditions of temperature and time to form an intermediate zinc dialkyl dithiophosphate product comprising basic and neutral salts, said intermediate product characterized as having a ratio of basic salt to neutral salt of from 0.075 to 0.75 as determined by $^{31}$P-NMR;

c) subsequent to step b), feeding from 1.5 to 5 weight percent based upon the charge of zinc oxide, of a promoter selected from the group consisting of formic acid, acetic acid, propionic acid, butyric acid, iso-butyric acid, pentanoic acid, 2-methyl-butyric acid, 3-methyl-butyric acid, and mixtures thereof to form a reaction mass; and d) reacting the reaction mass of step c) under suitable temperature and time to form an overbased zinc dialkyl dithiophosphate product characterized as having a sediment of less than 0.01 weight percent and a metal to phosphorous ratio of from 1.08 to 1.30.

Among other factors, the present invention is based in part on the unexpected discovery that a specified delayed addition of a particular promoter during neutralization of a particular group of dialkyl dithiophosphoric acids can dramatically reduce the resulting haze and or sediment of the final overbased metal dialkyl dithiophosphate product. Quite surprisingly, there is a particularity not only in the promoter type and degree of delay of the promoter, measured herein as the ratio of basic salt to neutral salt, as well as the type of dialkyl dithiophosphoric acid employed. This unique method and combination leads to a product having low crude sediment and a low degree of haze.

DETAILED DESCRIPTION OF THE INVENTION

The method for preparing the dialkyl dithiophosphoric acid for reaction with a metal oxide is not critical to the invention, and thus, any of the well known batch and continuous processes for the dithiophosphoric acid formation reaction may be used. Generally, one mole of phosphorus pentasulfide ($P_2S_5$) is reacted with about four equivalents of alcohol. Typically a minor excess of alcohol is employed.

Alcohol is charged to the reactor while heating to a temperature within the range of from about 55° C. to about 110° C., more preferably about 75° C. to about 100° C., and most preferably about 90° C. to about 100° C. It is preferred to use an excess of alcohol in the reaction mass, most preferably less than about 15 mole percent excess alcohol, more preferably less than 10 mole percent excess alcohol. Excess phosphorus sulfide in the reaction mass is generally to be avoided since there is a tendency to form undesirable by-products when there is an excess of $P_2S_5$. After the reaction is complete, the reactant mixture is cooled and preferably sparged with nitrogen or another inert gas to remove residual hydrogen sulfide to suitable levels. Removal of the residual hydrogen sulfide is thought to reduce the formation of metal sulfide precipitate in the subsequent neutralization step. Preferably the dialkyl dithiophosphoric acid product contains less than 200 parts per million residual hydrogen sulfide, more preferably less than 100 parts per million residual hydrogen sulfide, and most preferably less than 50 parts per million residual hydrogen sulfide.

The phosphorus sulfide reactant used in the dithiophosphoric acid formation step of this invention may be selected from any one or more of $P_4S_{10}$, $P_4S_9$, $P_4S_7$, $P_4S_3$, or mixtures of the foregoing, with the industry coined phosphorus pentasulfide being the most preferred. Commercially available phosphorous pentasulfide or $P_2S_5$ is primarily a mixture of $P_4S_{10}$ and $P_4S_9$ with lesser amount of $P_4S_7$, and phosphorous polysulfides ($P_mS_y$ where y/m>2.5). The amount of $P_4S_{10}$ and $P_4S_9$ contained in commercial $P_2S_5$ can be varied somewhat during the reaction process by adjusting the phosphorous to sulfur molar charge ratio. As the phosphorous level is decreased below the stoichiometric level of 27.87 weight percent for $P_4S_{10}$, the $P_2S_5$ mixture becomes richer in polysulfides and/or free sulfur and depleted in $P_4S_9$. As the phosphorous level is increased above 27.87 weight percent, the $P_4S_{10}$ and free sulfur content decrease, while the $P_4S_9$ and $P_4S_7$ levels increase. It has been postulated that overbased metal dialkyl dithiophosphate compositions prepared from a grade of $P_2S_5$ containing >27.87 weight percent P would have improved performance in copper corrosion tests (ASTM D 130) in comparison to those prepared from a grade of $P_2S_5$ containing <27.87 weight percent P. Therefore, particularly preferred $P_2S_5$ employed in this invention is the grade of $P_2S_5$ variety having a phosphorous level above 27.87 weight percent, preferably from about 27.9 weight percent to about 28.3 weight percent phosphorus. Improved performance in copper corrosion tests (ASTM D 130) can also be attained by treating the dithiophosphoric acid with sulfur scavengers such as triphenylphosphite.

Reactivity of $P_2S_5$ is influenced by both phosphorous: sulfur stoichiometry and the rate at which the $P_2S_5$ is cooled from the melt. Generally, the higher rate of cooling results in higher reactivity with alcohols. It is believed that the higher reactivity $P_2S_5$ is more amorphous in structure in contrast to the lower reactivity $P_2S_5$ which is more crystalline. Although reactivity of $P_2S_5$ increases somewhat with smaller particle size (increased surface area) the reactivity is mainly influenced by the rate at which the molten $P_2S_5$ is cooled.

While the formula of phosphorus pentasulfide is generally represented as $P_2S_5$, the actual structure is believed to an equilibrium mixture of $P_4S_{10}$, $P_4S_9$, $P_4S_7$, as well as others. However, for simplicity the dithiophosphoric acid reaction is often simplified as a reaction of $P_2S_5$ with an alcohol. Accordingly, one mole equivalent of $P_2S_5$ will react with four equivalents of a hydroxy compound to produce the dithiophosphoric acid. For the purposes of this invention, the phosphorus sulfide reactant can be considered as a compound having the formula of $P_2S_5$ with the understanding that the actual structure is much more complex.

The hydroxy compounds from which the dialkyl dithiophosphoric acids are derived can be represented generically by an alcohol having the formula ROH wherein R is hydrocarbyl or substituted hydrocarbyl group, and more particularly a substituted alkyl group. Particularly preferred R groups are alkyl groups of from 3 to 20 carbon atoms. Preferably the alcohol is a primary alcohol which is characterized by at least one —CH$_2$OH group and even more preferably a monohydroxy alcohol. Mixtures of hydroxy compounds may also be used. As is recognized in the art, these hydroxy compounds need not be monohydroxy compounds. That is, the dialkyl dithiophosphoric acids may be prepared from mono-, di-, tri-, and other polyhydroxy compounds, or mixtures of two or more of the foregoing.

Examples of the general class of compounds corresponding to the formula ROH are those wherein R is selected from an alkyl, cycloalkyl, alkyl-substituted cycloalkyl, arylalkyl, alkoxyalkyl, haloalkyl, and the like.

Of the foregoing, the aliphatic alcohols which include branched aliphatic alcohols are preferred. More preferred are the aliphatic alcohols having from 3 to 20 carbon atoms; and even more preferably primary alcohols having from 3 to 12 carbon atoms, even more preferably 6 to 8 carbon atoms. The alcohols may be monoalcohols such as propyl, butyl, pentyl, hexyl, heptyl, octyl, nonyl, decyl and the like. The alcohols may be straight chain or branched, and may contain unsaturation, and may be mixtures thereof.

Preferably the aliphatic alcohols are $C_3$ to $C_{12}$ primary alcohols. The preferred straight chain alcohols are propanol, butanol, pentanol, hexanol, heptanol, octanol, nonanol, decanol, undecanol, dodecanol and the like. Particularly preferred are branched chain primary alcohols with methyl, ethyl, propyl, and isopropyl branching or mixtures thereof. Such primary alcohols when the branch chain is a methyl group can be selected from the group consisting of methyl-1-pentanol, methyl-1-butanol, methyl-1-pentanol, methyl-1-hexanol, methyl-1-heptanol, methyl-1-octanol, methyl-1-nonanol and methyl-1-decanol. It being understood that the methyl group and/or the branching group can be at any carbon atom other than the alpha carbon. Particularly preferred are $C_6$ to $C_8$ primary alcohols such as methyl-1-pentanol, 2-ethyl butanol, methyl-1-hexanol, ethyl-1-pentanol, 2-ethyl-2-methyl-butanol, methyl-1-heptanol, 2-ethyl-1-hexanol, 2-propyl pentanol, ethyl-methyl-pentanol, dimethyl-1-pentanol or 2-isopropylpentanol. It is to be understood that most commercially available alcohols are not pure compounds but are mixtures containing a predominant amount of the desired alcohol and minor amounts of various isomers and/or longer or shorter chain alcohols.

The dithiophosphoric acid formation reaction is typically conducted under substantially anhydrous conditions, in the absence of solvent and/or catalyst. The reaction of the hydroxy compound with $P_2S_5$ is exothermic, and thus the heat of reaction can be used to aid in heating the reaction mixture. Also, the heat of reaction as well as external heating and/or cooling of the reactor can be employed to maintain the desired reaction temperature. Once the dialkyl dithiophosphoric acid reaction is complete, the dialkyl dithiophosphoric acid product is cooled and may be stripped with an inert gas such as nitrogen to remove residual hydrogen sulfide, preferably the concentration of hydrogen sulfide in the dithiophosphoric acid is less than 200 parts per million. If the hydrogen sulfide is not removed prior to neutralization with a metal oxide, the metal oxide can react with hydrogen sulfide to form a metal sulfide precipitate which can contribute to crude sediment. Additionally, the metal oxide that is converted to a metal sulfide is no longer available for the formation of the basic salt of a metal dithiophosphate, which results in less basic salt formation for a given metal oxide charge. Residual $P_2S_5$ in the dithiophosphoric acid preferably should be removed before neutralization with the metal oxide by utilizing any well know solid/liquid separation techniques such as gravity settling, centrifugation and filtration. If not removed, this residual $P_2S_5$ can react with the water formed during the dithiophosphoric acid neutralization reaction to form phosphoric acid and hydrogen sulfide. These compounds can react with the metal oxide compound during the neutralization process to form a precipitate.

The dialkyl dithiophosphoric acid is neutralized and overbased by contacting a metal oxide with the dialkyl dithiophosphoric acid, in the absence of a promoter or catalyst, to form an intermediate product comprising basic and neutral dialkyl dithiophosphate salts, said intermediate product characterized as having a ratio of basic salt to neutral salt of about 0.075 to about 0.75, wherein said ratio is determined by $^{31}$P-NMR analysis. Subsequent to the formation of this intermediate product, an aliphatic mono-carboxylic acid promoter having 1 to 5 carbon atoms is then added to form a reaction mass from 1.5 to 5 weight percent based upon the charge of metal oxide. Then, the reaction mass can be reacted under suitable temperature and time to form an overbased metal dialkyl dithiophosphate product characterized as having a crude sediment of less than 0.01 weight percent. The delayed addition of the mono-carboxylic acid until a substantial amount of the basic salt has been formed provides for reduced total product sediment when compared to the case when the promoter is added before or at the time of neutralization.

Preferably, a high purity metal oxide is employed for neutralizing the dialkyl dithiophosphoric acid. Acceptable metal oxides include the oxides of: bismuth, cobalt, chromium, copper, nickel, vanadium, tungsten and zinc. Preferred metal oxides are oxides of copper and zinc. A particularly preferred metal oxide is zinc oxide and preferably zinc oxide manufactured by the "French process". Zinc oxide prepared from the "American process" tends to cause color and/or additional sediment issues with the zinc dialkyl dithiophosphate product. Typically, zinc oxides produced by the French process contain fewer impurities and contain a finer particle size when compared to the American process. Particularly preferred zinc oxide has a surface area of greater than about 3 m$^2$ per gram, preferably from about 4 to about 10 m$^2$ per gram. Super fine or nanoparticle zinc oxide having 11 to 40 m$^2$ per gram may offer a further benefit since zinc particle size has been shown to influence the rate of neutralization with studies showing that increasing the surface area of the zinc oxide increases the neutralization rate. For easier handling, the bulk density of the zinc oxide can be increased by the formation of loose agglomerations of zinc oxide particles.

The metal oxide can be added to the neutralization reactor either as a slurry or a dry solid. When employed in a slurry, the metal oxide is suspended in a suitable liquid such as neutral oil or a portion of the total dithiophosphoric acid charge. The neutral oil when used is preferably a light lubricating oil since their lower viscosities generally ease handling and/or pumping requirements; however heavier oils may be used as well as synthetic oils. When applied as a dry solid, the metal oxide is added directly to the neutralization reactor, which contains either neutral oil, the total charge of dithiophosphoric acid to be neutralized or an initial portion or "heel" of the dithiophosphoric acid, which is of suitable quantity to slurry the metal oxide. Typically, the "heel" process is used if there is a limitation as to cooling capacity. Typically, a "heel" is roughly 20 to 50 volume percent of the total reaction volume and preferably 25 to 35 percent of the total reaction volume. Typically, the dithiophosphoric acid "heel" and optionally neutral oil are fed to the reactor followed by the appropriate amount of metal oxide under mixing conditions to form the slurry. An excess amount of neutral oil should be avoided since although this does improve material handling of the slurry it can adversely affect capacity and product yields. Water is to be avoided in preparation of the metal oxide slurry since added water has been shown to increase solids in the final product. To the heel process, the remaining dithiophosphoric acid charge is added once the metal oxide slurry is formed. Preferably the addition of the metal oxide to form the slurry is not delayed and typically is completed in less than one hour and more preferably less than thirty minutes. The amount of metal oxide used in the neutralization step is that amount sufficient to form the desired level of overbased metal salt of dialkyldithiophosphate. A particularly preferred overbased zinc dialkyl dithiophosphate composition has a zinc to phosphorus weight ratio of about 1.08:1 or higher, preferably 1.08:1 to 1.30:1, more preferably 1.1:1 to 1.22:1 and even more preferably about 1.14:1 to 1.18:1.

In any event, the dithiophosphoric acid and metal oxide is allowed to react under suitable neutralization conditions to form an intermediate product comprising of basic and neutral dialkyl dithiophosphate salts characterized as having a ratio of basic salt to neutral salts of about 0.075 to about 0.75 as measured by $^{31}$P-NMR analysis. The intermediate, and for that fact, final overbased dialkyldithiophosphate are comprised of "neutral" and "basic" metal salts of dithiophosphoric acid. The neutral metal salt is typically and over-simplistically described as the product of the reaction of one molar equivalent of a metal oxide (such as zinc oxide) with one molar equivalent of dithiophosphoric acid ((RO)$_2$P(S)SH) where R is an independently selected alkyl group and more preferably a branched chain alkyl group from three to twelve carbon atoms and even more preferably where the alpha carbon to the oxygen is methylene. However, there is evidence that the neutral salt can be a dimer of bridged form in equilibrium with a monomeric chelated structure, P. G. Harrison and T. Kikabhai, *J. Chem. Soc., Dalton Trans.* (1987), 807. Basic salts, in comparison to the simplistic neutral salt model, contain excess metal oxide, thus greater than stoichiometric amounts required for neutral salt formation. There is substantial evidence that the zinc dialkyldithiophosphate basic salt is a tetrahedral cage-like molecule comprised of three neutral salt molecules and one zinc oxide molecule.

Unexpectedly, it has been discovered that there is an equilibrium mixture of the basic and neutral salts that can be affected by process conditions. More particularly, if the neutralization reaction of the dialkyldithiophosphoric acid and metal oxide is initially reacted, in the absence of a $C_1$ to $C_5$ mono-carboxylic acid promoter, to form an intermediate product comprising basic and neutral dialkyl dithiophosphate salts, said intermediate product characterized as having a ratio of basic salt to neutral salt of about 0.075 to about 0.75, wherein said ratio is determined by $^{31}$P-NMR analysis, and thereafter adding to this intermediate product from 1.5 to weight percent, based upon the metal oxide charge, of an aliphatic mono-carboxylic acid promoter having 1 to 5 carbon atoms to form a reaction mass which then can be further reacted under suitable temperature and time to form an overbased metal dialkyldithiophosphate product characterized as having a crude sediment of less than 0.01 weight percent, whereby said overbased metal dialkyldithiophosphate product has a low sediment and low haze value.

The neutralization reaction temperature is preferably maintained above 50° C. to about 95° C. and more preferably from about 65° C. to about 85° C. During the dithiophosphoric acid addition, the reaction mass is typically controlled at a temperature within the range of from about 65° C. to about 85° C. by manipulating the rate of addition or by external cooling means. The rate of dithiophosphoric acid addition to the reaction mass is not critical to the invention and may range from 5 minutes to 3 hours or more. In general, depending on the reaction mass size and scale of reaction, the dithiophosphoric acid addition can generally be completed within about 1 to 2 hours. Typically, a slight negative pressure is maintained on the reactor during the neutralization, and any gases that are generated are vented to a waste gas system. After addition of all components, the reactor is held at reaction temperature until the neutralization reaction is complete, typically under 5 hours. In order to maintain the desired temperature during neutralization, the reaction vessel contents may be subjected to heating or cooling by the use of internal or external heating/cooling coils, reactor heating/cooling jackets, heat exchange circulation loops, and the like. After the reaction is complete, excess alcohol and water of neutralization can be removed by flash distillation. Preferably, a falling film or wiped film evaporator is used. Distillation using a single stage flash drum can also be employed.

Conventional $^{31}$P-NMR procedures are used to assay the amount of neutral or basic metal dialkyl dithiophosphate salt. The spectral positions are referenced to triphenylphosphate (−17.3 ppm). In accordance with these procedures for example, the basic species from a primary zinc dialkyl dithiophosphate appears in the range of about 103 to 105 ppm in the spectrum, whereas that derived from a secondary zinc dialkyl dithiophosphate appears in the range of about 98 to 100 ppm in the spectrum. On the other hand, the neutral species from a primary zinc dialkyl dithiophosphate appears in the range of about 100 to 102 ppm in the spectrum, whereas that derived from a secondary zinc dialkyl dithiophosphate appears in the range of about 92 to 94 ppm. The signals are integrated in the usual manner to calculate the relative amounts. These signals can also be used to give an overbased or basic salt to neutral salt ratio. This ratio can also be used to determine the appropriate time to add the delayed addition of a promoter to the dithiophosphoric acid and metal oxide intermediate product. Preferred ratios of basic to neutral salts are from 0.075 to 0.75, and more preferably the ratio of basic to neutral salts are from 0.1 to 0.5.

The mono carboxylic acid promoter is selected from hydrocarbyl mono-carboxylic acids containing from 1 to 5 carbon atoms, preferably from 1 to 3 carbon atoms. The preferred carboxylic acids are those having the formula RCOOH, wherein R is a straight or branched chain aliphatic groups (e.g. alkyl or alkenyl). Suitable acids include: formic acid, acetic acid, propionic acid, butyric acid, iso-butyric acid, pentanoic acid, 2-methyl-butyric acid, 3-methyl-butyric acid, as well as olefinic acids such as acrylic, methacrylic, 2- and 3-butenoic acid, 2-, 3- and 4-pentenoic acid. Particularly preferred branched chain acids include 2-methylbutanoic, 3-methylbutanoic, and the like. A particularly preferred carboxylic acid is selected from the group consisting of formic acid, acetic acid, propionic acid and butyric acid, more preferably from the group consisting of formic acid, acetic and propionic acid, with acetic acid being particularly preferred. The amount of mono-carboxylic acid employed as a promoter is less than 5 weight percent based upon the metal oxide charge, and preferably from about 1.5 weight percent to about 4 weight percent, and most preferably from about 1.5 weight percent to about 3 weight percent.

EXAMPLES

In order to further illustrate the advantages of this invention, the following illustrative examples are given. While the following examples illustrate specific embodiments of the present invention, they should not be interpreted as limitations upon the scope of the invention. Determination of weight percent used herein is outline in Example 4 below. Definitions and determination of haze as used herein are after Table 1.

Example 1

Charge 584.2 parts primary DTPA to stirred glass reactor. (DTPA was sparged with nitrogen to remove any residual $H_2S$ just prior to charging reactor.) 75.6 parts ZnO were charged to the reactor in 5 aliquots (approximately equal quantities) over 15 minutes while the DTPA was being stirred. Reaction mixture was heated to approximately 77° C. (Heating time ~15 minutes.) The reactor was then held at 77° C. for one hour. 1.5 parts acetic acid were then added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.009 weight percent and haze was 5.6 percent.

Example 2

Charge 206.8 parts primary DTPA to stirred glass reactor. (DTPA was sparged with nitrogen to remove any residual $H_2S$ just prior to charging reactor.) 80.4 parts ZnO were charged to the reactor in a single addition while the DTPA was being stirred. Reaction mixture was heated to approximately 77° C. Simultaneously, an additional 414.3 parts of the primary DTPA (same DTPA as above) were added to the reactor over a two hour period. 0.8 parts acetic acid was added to the reaction mixture upon completion of the DTPA addition. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.04 weight percent and the haze was too high to be measured (opaque).

Example 3

Charge 106.0 parts primary DTPA to stirred glass reactor. (DTPA was sparged with nitrogen to remove any residual $H_2S$ just prior to charging reactor.) 41.1 parts ZnO were charged to the reactor in a single addition while the DTPA was being stirred. Reaction mixture was heated to approximately 77° C. Simultaneously, an additional 211.8 parts of the primary DTPA (same DTPA as above) were added to the reactor over a one hour period. 0.8 parts acetic acid was then added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.002 weight percent and haze was 7.1 percent.

Example 4

Charge 96.8 parts primary DTPA to stirred glass reactor. (DTPA was sparged with nitrogen to remove any residual $H_2S$ just prior to charging reactor.) 37.5 parts ZnO were charged to the reactor in a single addition while the DTPA was being stirred. Reaction mixture was heated to approximately 77° C. Simultaneously, an additional 193 parts of the primary DTPA (same DTPA as above) were added to the reactor over a two hour period. 0.75 parts acetic acid was added to the reaction mixture upon completion of the DTPA charge. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.002 weight percent and haze was 8.9 percent.

Determination of weight percent sediment in the final product is outlined below. 97.3645 grams of the crude ZDTP were weighed into a clean, 150 mL centrifuge tube that had a tare weight of 140.7255 grams. A sufficient amount of reagent grade hexane was added to the centrifuge tube (~50 mL) fill the tube to within about a centimeter of the tube neck. The tube was sealed with a screw cap. The ZDTP/hexane mixture was then vigorously shaken to facilitate dissolution. Once the ZDTP was completely dissolved, the sample was centrifuged for 15 minutes at approximately 3500 G's. The liquid layer in the sample was then carefully decanted from the solids layer and discarded making sure that no solids were lost. Approximately 100 mL of reagent grade hexane was added to the remaining solids. The centrifuge tube was again sealed with the screw cap. The solids/hexane mixture was then vigorously shaken to facilitate dissolution of any ZDTP remaining on the solids. The sample was centrifuged at the same conditions as mentioned previously. The sample liquid was again carefully decanted and discarded. The remaining solids were washed twice more using this technique. After the final centrifugation and decantation, the centrifuge tube with the remaining solids was dried by placing it in a vacuum oven at 70° C. for approximately 30 minutes. The weight of the centrifuge tube with the dried solids was 140.7272 grams. The weight percent sediment was calculated using the following formula:

Weight Percent Sediment=[((tube & sediment weight)−(tube weight))/(sample weight)]×100; so that Weight Percent Sediment=[((140.7272)−(140.7255))/(97.3645)]×100=0.002 weight percent.

Example 5

Charge 392.5 parts primary DTPA to stirred glass reactor. (DTPA was sparged with nitrogen to remove any residual $H_2S$ just prior to charging reactor.) 50.8 parts ZnO were charged to the reactor in a single addition while the DTPA was being stirred. Heating of the reaction mixture to approximately 77° C. was initiated. (Heating time ~45 minutes.) 45 minutes after the completion of the ZnO addition, 1.0 parts acetic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.007 weight percent and haze was 9.7 percent.

Example 6

Charge 349.9 parts primary DTPA to stirred glass reactor. (DTPA was sparged with nitrogen to remove any residual $H_2S$ just prior to charging reactor.) 45.3 parts ZnO were charged to the reactor in a single addition while the DTPA was being stirred. Heating of the reaction mixture to approximately 77° C. was initiated. (Heating time ~15 minutes.) One hour after the completion of the ZnO addition, 1.1 parts propionic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.010 weight percent and haze was 5.8 percent.

COMPARATIVE EXAMPLES

Example A Comparative

Charge 210.5 parts primary DTPA (~2/3 of the total DTPA charged) to stirred glass reactor. (DTPA was sparged with nitrogen to remove any residual $H_2S$ just prior to charging reactor.) 40.9 parts ZnO were charged to the reactor in a single addition while the DTPA was being stirred. An additional 105.3 parts of the DTPA were charged to the reactor. Immediately upon completion of the DTPA addition, 0.8 parts acetic acid was added to the reaction mixture. Reaction mixture was heated to approximately 77° C. (Heating time ~5 minutes.) The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.02 weight percent and haze was 50.3 percent.

Example B Comparative

Charge 325.9 parts primary DTPA to stirred glass reactor. (DTPA was sparged with nitrogen to remove any residual $H_2S$ just prior to charging reactor.) 42.2 parts ZnO were charged to the reactor in a single addition while the DTPA was being stirred. Heating of the reaction mixture to approximately 77° C. was initiated. (Heating time ~30 minutes.) 30 minutes after the completion of the ZnO addition, 0.8 parts acetic acid was added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.016 weight percent and haze was 26.0 percent.

Example C Comparative

Charge 330.9 parts primary DTPA to stirred glass reactor. (DTPA was sparged with nitrogen to remove any residual $H_2S$ just prior to charging reactor.) 42.8 parts ZnO were charged to the reactor in five aliquots (approximately equal quantities) over 30 minutes while the DTPA was being stirred. Immediately upon completion of the ZnO addition, 0.9 parts acetic acid was added to the reaction mixture. Heating of the reaction mixture to approximately 77° C. was initiated 15 minutes after starting the ZnO addition. (Heating time ~20 minutes.) The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.022 weight percent and haze was 42.4 percent.

Example D Comparative

Charge 329.5 parts primary DTPA to stirred glass reactor. (DTPA was sparged with nitrogen to remove any residual $H_2S$ just prior to charging reactor.) 42.6 parts ZnO were charged to the reactor in a single addition while the DTPA was being stirred. Reaction mixture was heated to approximately 77° C. Immediately upon completion of the ZnO charge, 2.0 parts 2-ethyl-hexanoic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.084 weight percent and the haze was too high to be measured (opaque).

Example E Comparative

Charge 298.4 parts primary DTPA to stirred glass reactor. (DTPA was sparged with nitrogen to remove any residual $H_2S$ just prior to charging reactor.) 38.6 parts ZnO were charged to the reactor in a single addition while the DTPA was being stirred. Reaction mixture was heated to approximately 77° C. One hour after the completion of the ZnO addition, 1.9 parts 2-ethyl-hexanoic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.099 weight percent and the haze was too high to be measured (opaque).

Example F Comparative

Charge 146.2 parts secondary DTPA (MIBC based) to stirred glass reactor. (DTPA was sparged with nitrogen to remove any residual $H_2S$ just prior to charging reactor.) 20.5 parts ZnO were charged to the reactor in a single addition while the DTPA was being stirred. Reaction mixture was heated to approximately 77° C. (Heating time ~15 minutes.) 0.4 parts acetic acid was added to the reaction mixture about three minutes after the ZnO was charged. The reactor temperature was maintained at 77° C. for four hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.19 weight percent and haze was too high to be measured (opaque).

Example G Comparative

Charge 146.2 parts secondary DTPA (MIBC based) to stirred glass reactor. (DTPA was sparged with nitrogen to remove any residual $H_2S$ just prior to charging reactor.) 20.5 parts ZnO were charged to the reactor in a single addition while the DTPA was being stirred. Reaction mixture was heated to approximately 77° C. (Heating time ~15 minutes.) Reaction mixture was held at these conditions for 55 minutes. Immediately following this hold period, 0.4 parts acetic acid was added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.36 weight percent, and the haze was too high to be measured (opaque).

Example H Comparative

Charge 213.7 parts primary unfiltered/unstripped (crude) ZDTP to a stirred glass reactor. 55.3 parts ZnO were charged to the reactor in a single addition while the ZDTP was being stirred. 427.0 parts of the DTPA were charged to the reactor over a two hour period. Simultaneously, the reaction mixture was heated to approximately 77° C. (Heating time ~40 minutes.) Immediately upon completion of the DTPA addition, 1.1 parts acetic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.18 weight percent and the haze was too high to be measured (opaque).

Example I Comparative

Charge 230.9 parts primary unfiltered/unstripped (crude) ZDTP to a stirred glass reactor. 59.8 parts of ZnO were charged to the reactor in a single addition while the ZDTP was being stirred. 461.9 parts of the DTPA were charged to the reactor over a two hour period. Simultaneously, the reaction mixture was heated to approximately 77° C. (Heating time ~40 minutes.) One hour after the DTPA addition, 1.2 parts acetic acid were added to the reaction mixture. The reactor temperature was maintained at 77° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.215 weight percent and the haze was too high to be measured (opaque).

Example J Comparative

Charge 159.3 parts secondary DTPA (based on a blend of 2-Butanol and MIBC) to stirred glass reactor. (DTPA was sparged with nitrogen to remove any residual $H_2S$ just prior to charging reactor.) 78.6 parts ZnO were charged to the reactor in a single addition while the DTPA was being stirred. The reaction mixture temperature increased to 80° C. due to the heat of reaction. The reaction mixture then was cooled to about 50° C. using an ice bath. A second charge of the secondary DTPA was made over approximately a two hour period using a dropping funnel. Simultaneously, the reaction mixture was heated to approximately 76° C. 1.6 parts acetic acid were added to the reaction mixture upon completion of the DTPA addition. The reactor temperature was maintained at 76° C. for three hours. The reactor pressure was then reduced from atmospheric pressure to <50 mmHg (absolute). The reactor temperature was the increased to 99° C. over 30 minutes. The water of neutralization and any residual alcohol from the DTPA are removed overhead. The unfiltered product sediment was 0.14 weight percent and haze was too high to be measured (opaque).

TABLE 1

| Example No. | Slurry Material | Promoter Type | Delay Time (min.) | Intermediate Product Basic/Neutral Salt Ratio | Sediment (wt %) | Product Haze (%) | Zn/P Weight Ratio |
|---|---|---|---|---|---|---|---|
| 1 | 1-DTPA | A | 60 | — | 0.009 | 5.6 | 1.22 |
| 2 | 1-DTPA | A | 120 | — | 0.04 | Opaque | — |
| 3 | 1-DTPA | A | 60 | 0.111 | 0.002 | 7.1 | 1.21 |
| 4 | 1-DTPA | A | 120 | 0.133 | 0.002 | 8.9 | 1.22 |
| 5 | 1-DTPA | A | 45 | 0.153 | 0.007 | 9.7 | 1.23 |
| 6 | 1-DTPA | B | 60 | 0.429 | 0.010 | 5.8 | 1.25 |
| COMPARATIVE EXAMPLES | | | | | | | |
| A | 1-DTPA | A | 0 | 0 | 0.020 | 50.3 | 1.23 |
| B | 1-DTPA | A | 30 | 0.052 | 0.016 | 26.0 | 1.21 |

TABLE 1-continued

|   | Slurry Material | Promoter | | Intermediate Product | Product | | |
|---|---|---|---|---|---|---|---|
|   |   | Type | Delay Time (min.) | Basic/ Neutral Salt Ratio | Sediment (wt %) | Haze (%) | Zn/P Weight Ratio |
| C | 1-DTPA | A | 0 | 0 | 0.022 | 42.4 | 1.21 |
| D | 1-DTPA | C | 0 | 0 | 0.084 | Opaque | 1.26 |
| E | 1-DTPA | C | 60 | 0.58 | 0.099 | Opaque | 1.23 |
| F | 2-DTPA | A | 0 | 0 | 0.19 | Opaque | 1.14 |
| G | 2-DTPA | A | 60 | 0 | 0.36 | Opaque | 1.17 |
| H | 1-ZnDTP | A | 0 | 1.016 | 0.18 | Opaque | 1.24 |
| I | 1-ZnDTP | A | 60 | 1.532 | 0.215 | Opaque | 1.22 |
| J | 2-ZnDTP | A | 120 | — | 0.14 | Opaque | 1.11 |

Wherein in the table above the terms have the following definitions: 1-DTPA is a dialkyl dithiophosphoric acid derived from phosphorous pentasulfide and a primary alcohol; namely, 2-ethyl-1-hexanol. A typical process for preparing 1-DTPA is as follows: 120 parts of 2-ethyl-1-hexanol based DTPA were charged to a stirred glass reactor. 100 parts $P_2S_5$ were charged to the reactor in a single addition while the DTPA was being stirred. Reaction mixture was slowly heated to approximately 100° C. over an hour period. Simultaneously, 250.2 parts of 2-ethyl-1-hexanol were added to the reactor over approximately a two hour period. After 2-ethyl-1-hexanol addition was completed, the reactor temperature was maintained at 100° C. for 4.5 hours. The final product was cooled and then filtered using a Büchner filter with No. 2 Whatman paper. (2-DTPA is a dialkyl dithiophosphoric acid derived from phosphorous pentasulfide and a secondary alcohol; namely, 4-methyl-2-pentanol. A typical process for preparing 2-DTPA is as follows: Charge 272.2 parts MIBC (methylisobutylcarbinol) to a stirred glass reactor. The reactor was cooled to <4° C. using an ice bath. 403.3 parts $P_2S_5$ were charged to the reactor in a single addition while the MIBC was being stirred. The reaction mixture was slowly heated to approximately 82° C. over an hour period. Simultaneously, an additional 535.8 parts of MIBC were added to the reactor over approximately a two hour period. After MIBC addition was completed, the reactor temperature was maintained at 82° C. for 4.5 hours. The final product was cooled and then filtered using a Buchner filter with No. 2 Whatman paper. Promoter Type A is acetic acid, Type B is propionic acid, Type C is 2-ethylhexanoic acid. Intermediate Product—Basic/Neutral Salt Ratio is a ratio of the basic to neutral salts of the dithiophosphate in the reaction mixture (upon the full charge of reactants and just prior to the promoter addition) as measured by a determination and integration of its $^{31}$P-NMR spectrum. Haze was measured on a Nippon Denshoku Industries COH 300A instrument, which is used for the measurement of turbidity (haze) as well as transparent, Saybolt and ASTM colors. Such instrument is suitable for the following standards Turbidity (HAZE): ASTM D 1003, JIS K 010, JIS K 6714, JIS K 6717, JIS K 6718, JIS K 6774, JIS K 7105.

As illustrated by the Examples 1–6 above, delayed addition of the promoter until the formation of an intermediate product comprising basic and neutral dialkyl dithiophosphate salts, said intermediate product characterized as having a ratio of basic salt to neutral salt of about 0.075 to about 0.75, wherein said ratio is determined by $^{31}$P-NMR analysis, which upon further process steps results in an overbased metal dialkyl dithiophosphate product characterized as having a crude sediment before filtration of 0.01 weight percent or less. As further illustrated by the comparative examples, there is a particularity as to the type of promoter, the point of delayed addition as well as the type of dialkyl dithiophosphoric acid or the product "heel" of a zinc dialkyl dithiophosphate. Surprisingly, by careful consideration of the process components and process conditions the resulting product can be formed with low sediment and low haze. As demonstrated by Comparative Examples A–C if there is either no delay of the promoter or an incorrect amount of delay there is a dramatic increase in both sediments and haze in the resulting product. Additionally, as illustrated from Comparative Examples D and E, there is a dependence to the promoter type. Furthermore, Comparative Examples F–J show the relationship with the slurry material illustrating a particularity to the dialkyl dithiophosphoric acid derived from at least one $C_3$ to $C_{12}$ primary alcohol. Comparative Examples F and G show substantial sediment and haze when employing a dialkyl dithiophosphoric acid derived from a secondary alcohol, while Examples H–J shows high sediment and haze when employing a dithiophosphate product heel.

What is claimed is:

1. A process for the manufacture of a low sediment overbased metal dialkyl dithiophosphate composition comprising:
   a) reacting a phosphorous sulfide reactant with at least one $C_3$ to $C_{12}$ primary alcohol to form a dialkyl dithiophosphoric acid;
   b) neutralizing the dialkyl dithiophosphoric acid with a full charge of metal oxide for a sufficient amount of time, to form an intermediate product comprising basic and neutral dialkyl dithiophosphate salts, said intermediate product characterized as having a ratio of basic salt to neutral salt of about 0.075 to about 0.75, wherein said ratio is determined by $^{31}$P-NMR analysis;
   c) adding to the intermediate product from 1.5 to 5 weight percent based upon the metal oxide charge, of at least one aliphatic mono-carboxylic acid promoter having 1 to 5 carbon atoms to form a reaction mass; and
   d) reacting the reaction mass under suitable temperature and time to form an overbased metal dialkyl dithiophosphate product characterized as having a crude sediment before filtration of 0.01 weight percent or less.

2. The process of claim 1, wherein the metal of the metal oxide is selected from the group consisting of bismuth, cobalt, chromium, copper, nickel, vanadium, tungsten and zinc.

3. The process of claim 2, wherein the metal oxide is zinc oxide.

4. The process according to claim 1, wherein the phosphorous sulfide is a phosphorus pentasulfide having a phosphorous content from 27.9 to 28.3 weight percent.

5. The process according to claim 1, wherein prior to the neutralizing step the dialkyl dithiophosphoric acid undergoes sparging to remove residual hydrogen sulfide to less than 200 ppm.

6. The process according to claim 1, wherein the process is carried out in the absence of added process water.

7. The process of claim 1, wherein the dialkyl dithiophosphoric acid is derived from the reaction of phosphorous pentasulfide with a straight chain or branched chain $C_6$ to $C_8$ primary alcohol.

8. The process of claim 7, wherein the alcohol is 2-ethyl-1-hexanol.

9. The process of claim 1, wherein in the neutralizing step, the intermediate product is characterized as having a ratio of basic salt to neutral salt from 0.1 to 0.5 as determined by $^{31}P$ NMR prior to addition of the aliphatic mono-carboxylic acid promoter.

10. The process of claim 1, wherein during the neutralization step, the metal oxide is first slurried in a portion of the total amount of dialkyl dithiophosphoric acid.

11. The process of claim 1, wherein the aliphatic mono-carboxylic acid promoter is selected from the group consisting of formic acid, acetic acid, propionic acid, butyric acid, iso-butyric acid, pentanoic acid, 2-methyl-butyric acid, 3-methyl-butyric acid.

12. The process of claim 11, wherein the promoter is a mixture of aliphatic mono-carboxylic acids.

13. The process of claim 11, wherein the aliphatic mono-carboxylic acid is acetic acid.

14. The process of claim 1, wherein the alcohol is a mixture of $C_3$ to $C_{12}$ primary alcohols.

15. A process for the manufacture of a low sediment overbased zinc dialkyl dithiophosphate composition having a zinc to phosphorous weight ratio of from 1.08 to 1.30 comprising:
  a) forming a slurry of a full charge of zinc oxide in a full charge of a dialkyl dithiophosphoric acid derived from the reaction of phosphorous pentasulfide and at least one $C_3$–$C_{12}$ primary alcohol;
  b) reacting the slurry in a) under suitable conditions of temperature and time to form a intermediate zinc dialkyl dithiophosphate product comprising basic and neutral salts, said intermediate product characterized as having a ratio of basic salt to neutral salt of from 0.075 to 0.75 as determined by $^{31}P$-NMR;
  c) subsequent to step b), feeding from 1.5 to 5 weight percent, based upon the charge of zinc oxide, of a promoter selected from the group consisting of formic acid, acetic acid, propionic acid, butyric acid, iso-butyric acid, pentanoic acid, 2-methyl-butyric acid, 3-methyl-butyric acid, and mixtures thereof to form a reaction mass; and
  d) reacting the reaction mass of step c) under suitable temperature and time to form an overbased zinc dialkyl dithiophosphate product characterized as having a sediment of less than 0.01 weight percent and a zinc to phosphorous ratio of from 1.08 to 1.30.

16. The process of claim 15 wherein the process is carried out in the absence of added process water.

17. The process of claim 15, wherein in b), the ratio of basic to neutral salts of said intermediate dialkyl dithiophosphate is from 0.1 to 0.5 as determined by $^{31}P$-NMR.

18. The process of claim 17, wherein in b), the ratio of basic to neutral salts of said intermediate dialkyl dithiophosphate is from 0.1 to 0.3 as determined by $^{31}P$ NMR.

19. The process according to claim 15, wherein the phosphorus pentasulfide has a phosphorous content from 27.9 to 28.3 weight percent.

20. The process according to claim 15, wherein prior to the reacting the slurry step (b), the dialkyl dithiophosphoric acid undergoes sparging to remove residual hydrogen sulfide to less than 200 ppm.

21. The process of claim 15, wherein the dialkyl dithiophosphoric acid is derived from the reaction of phosphorous pentasulfide with a straight chain or branched chain $C_6$ to $C_8$ primary alcohol.

22. The process of claim 21, wherein the alcohol is 2-ethyl-1-hexanol.

23. The process of claim 15, wherein the promoter is selected from the group consisting of formic acid, acetic acid and proprionic acid.

24. The process of claim 21, wherein the promoter is acetic acid.

25. The process of claim 23, wherein the promoter is added from 1.5 to 3 weight percent.

26. The process of claim 15, wherein the overbased zinc dialkyl dithiophosphate composition has a metal to phosphorous weight ratio of from 1.1 to 1.22.

* * * * *